United States Patent
Galinis et al.

[11] Patent Number: 6,093,389
[45] Date of Patent: Jul. 25, 2000

[54] METHODS AND COMPOSITIONS FOR ATTRACTING AND CONTROLLING TERMITES

[75] Inventors: Deborah L. Galinis; Sven P. Strnad, both of Yardley, Pa.

[73] Assignee: American Cyanamid Company, Madison, N.J.

[21] Appl. No.: 08/980,587

[22] Filed: Dec. 1, 1997

Related U.S. Application Data

[60] Provisional application No. 60/031,549, Dec. 3, 1996.

[51] Int. Cl.[7] .......................... A01N 45/00; A01N 43/54; A01N 65/00
[52] U.S. Cl. ..................... 424/84; 424/484; 424/195.1; 424/DIG. 11; 514/169; 514/170; 514/171; 514/177; 514/178; 514/179; 514/180; 514/181; 514/182; 514/256; 514/263; 514/264; 514/275
[58] Field of Search .............................. 424/84, DIG. 11, 424/484, 195.1; 514/169, 170, 171, 177–182, 263, 264, 256, 275

[56] References Cited

U.S. PATENT DOCUMENTS

| | | | |
|---|---|---|---|
| 3,901,896 | 8/1975 | Albright | 260/288 |
| 4,452,793 | 6/1984 | Prestwich | 424/238 |
| 4,891,367 | 1/1990 | Angelastro et al. | 514/178 |
| 5,023,250 | 6/1991 | Adams et al. | 514/179 |
| 5,024,832 | 6/1991 | Omata et al. | 424/84 |
| 5,149,526 | 9/1992 | Sonenshine et al. | 424/84 |
| 5,246,936 | 9/1993 | Treacy et al. | 514/256 |
| 5,329,726 | 7/1994 | Thorne et al. | 43/124 |
| 5,555,672 | 9/1996 | Thorne et al. | 43/124 |
| 5,573,760 | 11/1996 | Thorne et al. | 424/84 |

FOREIGN PATENT DOCUMENTS

| | | |
|---|---|---|
| 271357 | 8/1991 | Czechoslovakia . |
| 0 276 823 B1 | 8/1988 | European Pat. Off. . |
| 0 562 849 A2 | 9/1993 | European Pat. Off. . |
| 0 587 117 A1 | 3/1994 | European Pat. Off. . |
| 0 590 489 A2 | 4/1994 | European Pat. Off. . |
| 53137931 | 12/1979 | Japan . |
| 528616 | 11/1993 | Japan . |
| 1197238 | 7/1970 | United Kingdom . |
| WO 92/15604 | 9/1992 | WIPO . |
| WO 94/16709 | 8/1994 | WIPO . |
| WO 94/28904 | 12/1994 | WIPO . |

OTHER PUBLICATIONS

Chemical Abstracts 117: 170987 (1992).
Chemical Abstracts 124: 281915 (1996).
Sokolov et al., "Structure—Activity Relationships in a Series of Polyhydroxysteroids," Dokl. Akad. Navk Belarusi, vol. 39(2), 1995, pp. 52–55.
Chemical Abstracts 124: 281916 (1996).
Bykhovets et al., "Biological Activity of Polyhydroxysteroids," Vestsi Akad. Navuk Belarusi, Ser. Biyal. Navuk, vol. 1, 1995, pp. 54–58.
Smythe, R.V. et al. J. Econ. Entomol. 1967, 60, 228–233.
Matsumara, F. Et al. Nature, 1968, 219, 963–964.
Tokoro, M., et al. Wood Research, 1989, No. 76, 29–38.
V. Varma, et al. KFRI Res. Rep., (Kerala For. Res. Inst., Peechi, Kerala, India) 1981, No. 6, 283–290.
Klochov, S.G. et al. Khim. Phir. Soedin. 1989, 3, 416–419, Chem. Abstr. 1989, 111, 93946m.
Cordeiro, M. et al. .J. Org. Chem., 1990, 55, 2806–2813.
Akisha, T. et al.Phytochemistry, 1994, 35, 1309–1313.
S. Kalra et al., Tetrahedron Letters, 1994, 35, 4847–4850.
Mauldin et al., Ann. Entomol. Soc. Am., 68(3), pp. 454–456 (1975).
Chemical Abstracts 83:25334 (1975) "Sterols in the termite *Nasutitermes rippertii*", K. Ubik, et al.
Chemical Abstracts 83:26741 (1975), "Rearing the subterranean termites *Reticulitermes flavipes* and *Coptotermes formosanus,* on artificial diets", J.K. Mauldin, et al.
Chemical Abstracts 102:76028 (1985) "Chemical composition of termites", Z. Jian, et al.

*Primary Examiner*—John Pak
*Attorney, Agent, or Firm*—Timothy J. Babcock

[57] ABSTRACT

The present invention provides a composition for attracting termites containing a steroid derivative of formula I

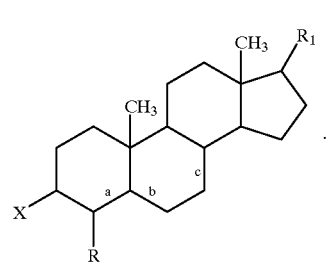

The present invention also provides a method for attracting or controlling termites with the composition.

22 Claims, No Drawings

METHODS AND COMPOSITIONS FOR ATTRACTING AND CONTROLLING TERMITES

This application claims priority from U.S. provisional application(s) Ser. No. 60/031,549 filed on Dec. 3, 1996.

BACKGROUND OF THE INVENTION

Termites cause hundreds of millions of dollars in damage to buildings each year. In the past, and to a lesser extent today, toxicants were used in an indiscriminate manner to prevent termite infestation. More recently, monitoring compositions have been developed to detect termite infestation.

Termite monitoring compositions require the use of decayed or fungus inoculated wood to attract termites. However, decayed or fungus inoculated wood is not entirely satisfactory for use on a commercial scale. In particular, it is difficult to source decayed wood which consistently meets all of the specifications for a commercial product. What is needed in the art is a termite attractant which is readily available in consistent form.

Certain compounds have been identified which cause trail-following behavior in termites. However, those compounds have not been shown to attract termites to bait compositions. U.S. Pat. No. 4,452,793 discloses certain 29-fluorophytosterol termiticides which may attract termites. However, none of the compounds described in that patent are within the scope of the present invention.

It is, therefore, an object of the present invention to provide a method for attracting termites to a composition without requiring the use of decayed or fungus inoculated wood.

It is also an object of the present invention to provide a method for controlling termites which avoids the indiscriminate use of large quantities of toxicants.

Those and other objects of the present invention will become more apparent from the detailed description thereof set forth below.

SUMMARY OF THE INVENTION

The present invention comprises a composition having a termite attractant in combination with one or more additives. The termite attractant is described in formula I, below. While each formula I compound is disclosed as a termite attractant, it is to be understood that all or a portion of each compound may provide the chemical properties for attracting a termite.

The additives can be, e.g., either one, or a combination of some or all of a pesticide, bait matrix, and excipient. A pesticide, either alone or in combination with a bait matrix, is preferred. Examples of a pesticide include an insecticide, e.g., a slow-acting toxicant, insect growth regulant and juvenile hormone accelerator. In combination with a pesticide and optionally with a bait matrix, the composition is useful as an insecticide.

When used in combination with a bait matrix, it is preferred that the slow-acting toxicant be nonrepellent to the insect and be either slow acting or have a delayed action. The slow-acting toxicant can also be either or both coated with a nonrepellent material and encapsulated, e.g., with a gelatinous or time release material.

Alternatively, either alone or in combination with a bait matrix, the composition is useful in the collection of termites, e.g., for zoological or other investigational studies.

Either alone, or in combination with either or both a pesticide and bait matrix, the composition is useful as a food source. A termite, and indeed most insects, are generally known to be a ready source of protein.

The present invention also describes a method for attracting termites which comprises providing the termites with a termite attractive amount of a steroid derivative having the structural formula I

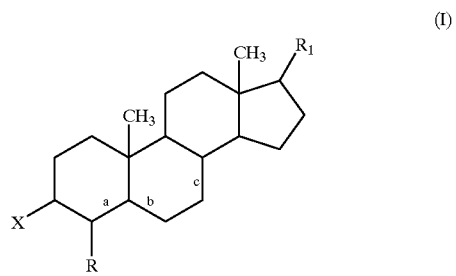

wherein

X is $AR_2$, oxo or thioxo;

$R_1$ is hydrogen, $A_1R_3$, oxo, thioxo,
—$CH(R_4)CH_2CH_2CH(R_5)CHR_6R_7$,
—$CH(R_4)CH$=$CHCH(R_5)CHR_6R_7$,
—$CH(R_4)CH_2CH_2C(CHR_6R_7)$=$CHR_5$, or
—$CH(R_4)CH$=$CHC(CHR_6R_7)$=$CHR_5$;

A and $A_1$ are each independently O or S;

R, $R_2$, $R_3$ and $R_5$ are each independently hydrogen or $C_1$–$C_4$alkyl; and $R_4$, $R_6$ and $R_7$ are each independently $C_1$–$C_4$alkyl;

provided that one of the bonds designated as a, b or c is a double bond and the other designated bonds are single bonds, and the optical isomers thereof, and the cis and trans isomers thereof.

The compounds in formula I are disclosed in the prior art. They have been disclosed as useful, e.g., in the treatment of androgen-dependent disorders and hypercholesterolemia.

The present invention further describes a method for controlling termites which comprises providing the termites with a composition comprising a pesticidally effective amount of a pesticide and a termite attractive amount of a steroid derivative of formula I.

The present invention still further describes a composition for monitoring and/or controlling termites which comprises a termite attractive amount of a steroid derivative of formula I.

DETAILED DESCRIPTION OF THE INVENTION

It has been found that termites are attracted to compositions containing a steroid derivative of formula I.

Preferred termite attractants of formula I are those wherein

X is OH or oxo;

R is hydrogen or $C_1$–$C_4$alkyl;

$R_1$ is hydrogen, OH, oxo,
—$CH(CH_3)CH_2CH_2CH(R_5)CH(CH_3)_2$,

—CH (CH$_3$)CH=CHCH(R$_5$)CH(CH$_3$)$_2$,

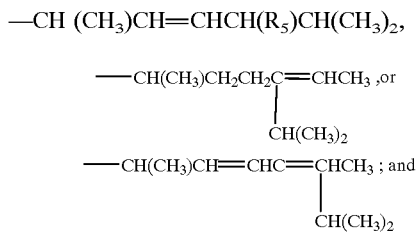

R$_5$ is hydrogen or C$_1$–C$_3$ alkyl;

provided that one of the bonds designated as a, b or c is a double bond and the other designated bonds are single bonds, and the optical isomers thereof, and the cis and trans isomers thereof.

More preferred termite attractants of the present invention are those having the structural formula I wherein X is OH or oxo;

R is hydrogen or methyl;

R$_1$ is hydrogen, OH, oxo,
—CH(CH$_3$)CH$_2$CH$_2$CH(R$_5$)CH(CH$_3$)$_2$,
—CH(CH$_3$)CH=CHCH(R$_5$)CH(CH$_3$)$_2$, or

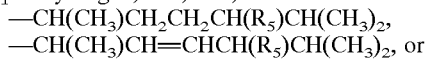

R$_5$ is hydrogen, methyl or ethyl;

provided that one of the bonds designated as a, b or c is a double bond and the other designated bonds are single bonds, and the optical isomers thereof, and the cis and trans isomers thereof.

Formula I compounds of the present invention which are particularly effective termite attractants include 3β-hydroxyandrost-5-en-17-one;

4β-methylstigmasta-7,24(28)-dien-3-one;

stigmast-4-en-3-one;

cholest-5-en-3β-ol;

androst-4-ene-3,17-dione;

androst-4-ene-3β,17β-diol;

stigmasta-4,22-dien-3-one; and androst-5-en-3β-ol, among others.

Advantageously, it has been found that decayed and fungus inoculated wood are not required to obtain a termite attractive composition.

The term "attractant" as used herein is defined as a compound that foraging termites find especially pleasing and stimulates the termites to locate compositions containing the compound over other compositions and/or their regular food source. The attractant may also stimulate foraging termites to feed on compositions containing the attractant over other compositions and/or their regular food source.

Advantageously, foraging termites will readily feed on a composition containing a steroid derivative of formula I, return to the nest to share the composition with other termites and recruit other termites to feed on the composition. The compositions of the present invention may be used to monitor for termite activity or, if a pesticide is incorporated into the composition, may be used to eliminate a termite infestation. The compositions of the present invention are especially useful for monitoring termite activity and/or eliminating termite infestations when they are formulated as bait compositions.

The bait compositions of the present invention preferably contain a cellulose source for the termites to consume. The cellulose source is an important component in the bait compositions of this invention because it serves as the food source for the termites. A highly palatable cellulose source is desirable because termites will readily feed on a bait composition containing it. The cellulose source of the present invention includes highly palatable cellulose sources such as wood, ground-up wood, sawdust, processed or purified cellulose and/or derivatives of cellulose such as methoxylated cellulose. Processed or purified cellulose is preferred, with microcrystalline or microgranular cellulose being more preferred.

In addition to cellulose, termites usually need moisture and nitrogen and, therefore, the bait compositions of this invention preferably include water and an exogenous nitrogen source utilizable by termites, such as urea, uric acid, amino acids, peptides, proteins and the like. The compositions of this invention may optionally contain a suitable binding medium including nutrient mediums such as agar, an agar/water gel mixture and the like, or a binding agent such as lignin sulfonate and the like.

When termite control is desired, a pesticide is incorporated into the compositions of this invention. Pesticides suitable for use in the compositions of this invention include, but are not limited to, slow-acting toxicants, insect growth regulators, pathogens and the like. A slow-acting toxicant or pesticide is preferable because the termites gathering the food then bring the termiticide back to the colony and transfer it to colony members that have not fed directly on the composition, thus reducing the size of the colony. A particularly useful pesticide in the practice of this invention is a termiticide such as hydramethylnon. Other slow-acting toxicants include, but are not limited to: sulfluramid, abamectin, fipranil, boric acid, a borate salt or ester, spinosid, imidacloprid, mirex and chlorfenapyr. Examples of insect growth regulants include, but are not limited to: flufenoxuron, teflubenzuron, diflubenzuron, hexaflumuron, lufenuron, pyripoxyfen, hydrophene, methoprene, fenoxycarb and a diacylhydrazine, e.g. as disclosed in U.S. Pat. No. 4,985,461 issued Jan. 15, 1991; U.S. Pat. No. 5,117,057 issued May 26, 1992; U.S. Pat. No. 5,354,762 issued Oct. 11, 1994 and U.S. Pat. No. 5,424,333 issued Jun. 13, 1995, and European patent 228,564 granted Jan. 29, 1992, all of which are incorporated herein by reference. Another pesticide can be a juvenile hormone accelerator.

Bait compositions of the present invention which are particularly useful for monitoring and/or controlling termites comprise, on a weight basis, about 20% to 85% of a cellulose source, about 1% to 10% of an exogenous nitrogen source, about 10% to 75% water, 0% to about 1% of a pesticide and about 0.000% to 1% of a steroid derivative of formula I.

The bait compositions of this invention may be prepared by blending a steroid derivative of formula I with a cellulose source, an exogenous nitrogen source and, optionally, a pesticide to form a dry blend. Water is then added to the dry blend and the resultant mixture is stirred to obtain the desired bait composition. Alternatively, the dry blend may be utilized directly in the target area without the addition of any water. Under those conditions, the environment supplies moisture through rain, humidity and the like. While termites prefer the moisture, they will still consume the dry product but to a lesser extent.

In a preferred embodiment of the present invention, the bait composition is placed into a cartridge that is perforated with at least one hole. The cartridge is then placed into a housing that is also perforated with at least one hole such that at least one hole in the cartridge is at least partially aligned with one hole in the housing to allow termites access to the bait composition. The housing is positioned for use by placing it in the soil or fixing it to a structure. In practical use, a first cartridge containing a bait composition which does not contain a pesticide is placed in the housing and used to monitor termite activity. If termite activity is detected in the monitoring composition, the first cartridge is removed from the housing and replaced with a second cartridge containing a bait composition which contains a pesticide.

The termite attractive amount of a steroid derivative present in a composition of this invention will depend upon a variety of factors such as the termite species to be monitored and/or controlled, the environment in which the composition is placed and the attractiveness of the particular steroid derivative present in the composition. In general, bait compositions comprising, on a weight basis, about 0.0001% to 1%, preferably about 0.001% to 0.1%, of a steroid derivative of formula I are attractive to termites.

The compositions of this invention are useful for attracting a variety of termites including, but not limited to, subterranean termites such as Reticulitermes flavipes (Kollar), Heterotermes aureus (Snyder), Reticulitermes hesperus Banks and Reticulitermes virginicus (Banks); dry-wood termites such as Kalotermes minor, Kalotermes snyderi Light, Kalotermes schwarzi Banks and Procryptotermes hubbardi (Banks); damp-wood termites such as Prorhinotermes simplex (Hagen); rotten-wood termites such as Zootermopsis angusticollis (Hagen) and Zootermopsis nevadensis (Hagen); powder-post termites such as Cryptotermes brevis (Walker); and nasutiform termites such as Nasutitermes corniger (Motschulsky). The compositions of this invention are especially useful for attracting subterranean termites such as Reticulitermes flavipes (Kollar).

The steroid derivatives of this invention are known in the art. See, e.g., the disclosures in the following patents and applications: U.S. Pat. Nos. 3,901,896; 4,891,367; 5,023,250; EP 276,823-A2; EP 562,849-A2; EP 590,489-A2; GB 1,197,238-A; WO 92/15,604; WO 94/16,709; and WO 94/28,904, and Tetrahedron Letters, 35, pp. 4847–4850 (1994). The disclosures in these citations are incorporated herein by reference. In addition, steroid derivatives of formula I wherein X and/or $R_1$ are thioxo may be prepared from formula I compounds wherein X and/or $R_1$ are oxo using Lawesson's reagent.

In order to facilitate a further understanding of the present invention, the following example is presented primarily for the purpose of illustrating more specific details thereof. The invention is not to be deemed limited thereby except as defined in the claims.

EXAMPLE 1

Evaluation of attractant activity of test compounds

The response of termites to test compounds is evaluated using a two choice assay. The arena for the assay is constructed from a 15 cm plastic petri dish. Two 1.5 cm holes are cut into the bottom of the petri dish about 11 cm opposite from one another and covered with a plastic slide cover (22×22 mm). Four vial caps (2.7 cm diameter×1.1 cm high) are inverted and placed under the petri dish. Two of the vial caps are placed under the holes in the petri dish and the other vial caps are used to balance the petri dish.

The test compounds are dissolved in dichloromethane, acetone or methanol to provide test solutions containing 0.1 mg or 1.0 mg of test compound per 200 μL of test solution. Two hundred μL of the appropriate test solution is placed on a small piece of filter paper and allowed to dry for ten minutes. A second piece of filter paper is treated with 200 μL of the appropriate solvent and allowed to dry for ten minutes. After the filter papers are dry, they are separately placed into the vial caps positioned under the holes in the petri dish. The vial cap containing the test compound is designated as the test vial cap and the vial cap containing the dried, solvent-treated filter paper is designated as the control vial cap.

A circle of damp filter paper (7.0 cm diameter) is placed in the center of the petri dish. Twenty Reticulitermes flavipes (Kollar) worker termites are placed on the damp filter paper and allowed to settle for ten minutes. The plastic slide covers are then removed to expose the holes and a lid is placed on the petri dish. After twenty minutes, the number of termites in each vial cap is counted and reported in Table I. If the number of termites in the test vial cap is greater than the number of termites in the control vial cap, the test compound is a termite attractant.

Compounds employed in this evaluation are given a compound number and identified by name. Data in Table I are reported by compound number.

| COMPOUNDS EVALUATED AS TERMITE ATTRACTANTS | |
|---|---|
| Compound Number | |
| 1 | 3β-Hydroxyandrost-5-en-17-one |
| 2 | 4β-Methylstigmasta-7,24(28)-dien-3-one |
| 3 | Stigmast-4-en-3-one |
| 4 | Cholest-5-en-3β-ol |
| 5 | Androst-4-ene-3,17-dione |
| 6 | Androst-4-ene-3β,17β-diol |
| 7 | Stigmasta-4,22-dien-3-one |
| 8 | Androst-5-en-3β-ol |

TABLE I

Attractant Activity of Test Compounds

| | | Number of Termites | |
|---|---|---|---|
| Compound Number | Amount of Compound in Test Vial Cap (mg) | Control Vial Cap | Test Vial Cap |
| 1 | 1.0 | 0 | 19 |
| 2 | 1.0 | 0 | 19 |
| 3 | 1.0 | 0 | 17 |
| 4 | 1.0 | 0 | 10 |
| 5 | 0.1 | 0 | 6 |
| 6 | 0.1 | 0 | 5 |
| 7 | 1.0 | 0 | 4 |
| 8 | 1.0 | 4 | 15 |

While the composition and method of using it is disclosed as a termite attractant, it is to be understood that the composition and method can be useful as an attractant for other wood using or wood attacking insects. These other insects include carpenter ants or bees, other bees, such as yellow jackets, and powder post beetles. As a general statement, each formula I compound can be an attractant for an insect selected from the group consisting of coleoptera, hymenoptera and isoptera.

We claim:

1. A method for attracting termites to a composition which comprises placing a composition comprising a termite attractive amount of a compound having the structural formula

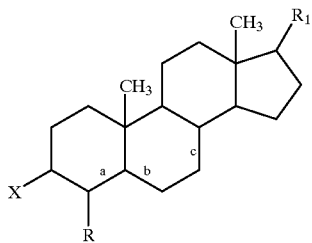

wherein

X is $AR_2$, oxo or thioxo;

$R_1$ is hydrogen, $A_1R_3$, oxo, thioxo,
—$CH(R_4)CH_2CH_2CH(R_5)CHR_6R_7$,
—$CH(R_4)CH=CHCH(R_5)CHR_6R_7$,
—$CH(R_4)CH_2CH_2C(CHR_6R_7)=CHR_5$, or
—$CH(R_4)CH=CHC(CHR_6R_7)=CHR_5$;

A and $A_1$ are each independently O or S;

R, $R_2$, $R_3$ and $R_5$ are each independently hydrogen or $C_1$–$C_4$alkyl; and $R_4$, $R_6$ and $R_7$ are each independently $C_1$–$C_4$alkyl;

provided that one of the bonds designated as a, b or c is a double bond and the other designated bonds are single bonds, and the optical isomers thereof, and the cis and trans isomers thereof, at a locus where foraging termites may be present.

2. The method according to claim 1 wherein

X is OH or oxo;

$R_1$ is hydrogen, OH, oxo,
—CH ($CH_3$)$CH_2CH_2CH(R_5)CH(CH_3)_2$,
—$CH(CH_3)CH=CHCH(R_5)CH(CH_3)_2$,

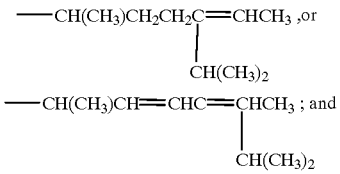

$R_5$ is hydrogen or $C_1$-$C_3$alkyl.

3. The method according to claim 2 wherein

R is hydrogen or methyl;

$R_1$ is hydrogen, OH, oxo,
—$CH(CH_3)CH_2CH_2CH(R_5)CH(CH_3)_2$,
—$CH(CH_3)CH=CHCH(R_5)CH(CH_3)_2$, or

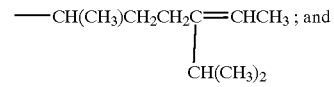

$R_5$ is hydrogen, methyl or ethyl.

4. The method according to claim 3 wherein the compound is selected from the group consisting of 3β-hydroxyandrost-5-en-17-one;

4β-methylstigmasta-7,24(28)-dien-3-one;

stigmast-4-en-3-one;

cholest-5-en-3β-ol;

androst-4-ene-3,17-dione;

androst-4-ene-3β,17β-diol;

stigmasta-4,22-dien-3-one; and androst-5-en-3β-ol.

5. The method according to claim 1 wherein the composition further comprises a cellulose source, an exogenous nitrogen source and water.

6. A method for controlling termites which comprises placing a composition comprising a pesticidally effective amount of a pesticide and a termite attractive amount of a compound having the structural formula

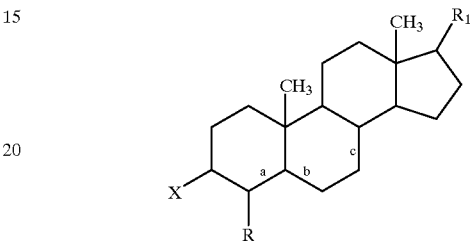

wherein

X is $AR_2$, oxo or thioxo;

$R_1$ is hydrogen, $A_1R_3$, oxo, thioxo,
—$CH(R_4)CH_2CH_2CH(R_5)CHR_6R_7$,
—$CH(R_4)CH=CHCH(R_5)CHR_6R_7$,
—$CH(R_4)CH_2CH_2C(CHR_6R_7)=CHR_5$, or
—$CH(R_4)CH=CHC(CHR_6R_7)=CHR_5$;

A and $A_2$ are each independently O or S;

R, $R_2$, $R_3$ and $R_5$ are each independently hydrogen or $C_1$–$C_4$alkyl; and $R_4$, $R_6$ and $R_7$ are each independently $C_1$–$C_4$alkyl;

provided that one of the bonds designated as a, b or c is a double bond and the other designated bonds are single bonds, and the optical isomers thereof, and the cis and trans isomers thereof, at a locus where foraging termites may be present.

7. The method according to claim 6 wherein

X is OH or oxo;

$R_1$ is hydrogen, OH, oxo,
—$CH(CH_3)CH_2CH_2CH(R_5)CH(CH_3)_2$,
—$CH(CH_3)CH=CHCH(R_5)CH(CH_3)_2$,

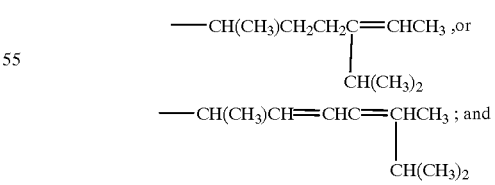

$R_5$ is hydrogen or $C_1$–$C_3$alkyl.

8. The method according to claim 7 wherein

R is hydrogen or methyl;

$R_1$ is hydrogen, OH, oxo,
—$CH(CH_3)CH_2CH_2CH(R_5)CH(CH_3)_2$,

—CH(CH₃)CH=CHCH(R₅)CH(CH₃)₂, or

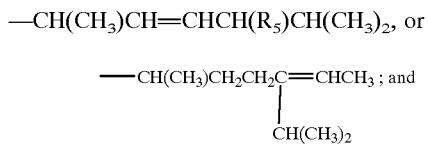

R₅ is hydrogen, methyl or ethyl.

9. The method according to claim 8 wherein the compound is selected from the group consisting of 3β-hydroxyandrost-5-en-17-one;
4β-methylstigmasta-7,24(28)-dien-3-one;
stigmast-4-en-3-one;
cholest-5-en-3β-ol;
androst-4-ene-3,17-dione;
androst-4-ene-3β,17β-diol;
stigmasta-4,22-dien-3-one; and
androst-5-en-3β-ol.

10. The method according to claim 6 wherein the pesticide is hydramethylnon.

11. The method according to claim 6 wherein the composition further comprises a cellulose source, an exogenous nitrogen source and water.

12. A composition for attracting and controlling termites which comprises a pesticidally effective amount of a pesticide and an effective termite attractive amount of a compound having the structural formula

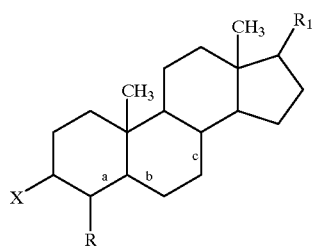

wherein
X is AR₂, oxo or thioxo;
R₁ is hydrogen, A₁R₃, oxo or thioxo,
—CH(R₄)CH₂CH₂CH(R₅)CHR₆R₇,
—CH(R₄)CH=CHCH(R₅)CHR₆R₇,
—CH(R₄)CH₂CH₂C(CHR₆R₇)=CHR₅, or
—CH(R₄)CH=CHC(CHR₆R₇)=CHR₅;
A and A₁ are each independently O or S;
R, R₂, R₃ and R₅ are each independently hydrogen or C₁–C₄alkyl; and
R₄, R₆ and R₇ are each independently C₁–C₄alkyl;
provided that one of the bonds designated as a, b or c is a double bond and the other designated bonds are single bonds, and
the optical isomers thereof, and
the cis and trans isomers thereof.

13. The composition according to claim 12 which further comprises a cellulose source, an exogenous nitrogen source and water.

14. The composition according to claim 13 which comprises, on a weight basis, about 20% to 85% of the cellulose source, about 1% to 10% of the exogenous nitrogen source, about 10% to 75% water, 0% to about 1% of the pesticide and about 0.0001% to 1% of the compound.

15. The composition according to claim 14 wherein the cellulose source is processed or purified cellulose, the exogenous nitrogen source is uric acid, and the pesticide is hydramethylnon.

16. The composition according to claim 12 wherein the pesticide is hydramethylnon.

17. The composition according to claim 12 wherein
X is OH or oxo;
R₁ is hydrogen, OH, oxo,
—CH(CH₃)CH₂CH₂CH(R₅)CH(CH₃)₂,
—CH(CH₃)CH=CHCH(R₅)CH(CH₃)₂,

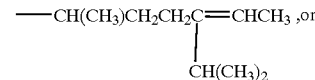

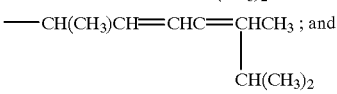

R₅ is hydrogen or C₁–C₃alkyl.

18. The composition according to claim 17 wherein
R is hydrogen or methyl;
R₁ is hydrogen, OH, oxo, —CH(CH₃)CH₂CH₂CH(R₅)CH(CH₃)₂, —CH(CH₃)CH=CHCH(R₅)CH(CH₃)₂, or

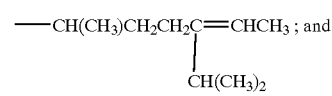

R₅ is hydrogen, methyl or ethyl.

19. The composition according to claim 18 wherein the compound is selected from the group consisting of
3β-hydroxyandrost-5-en-17-one;
4β-methylstigmasta-7,24(28)-dien-3-one;
stigmast-4-en-3-one;
cholest-5-en-3β-ol;
androst-4-ene-3,17-dione;
androst-4-ene-3β,17β-diol;
stigmasta-4,22-dien-3-one; and
androst-5-en-3β-ol.

20. A composition comprising an insecticide; an effective termite attractive amount of a compound having the structural formula

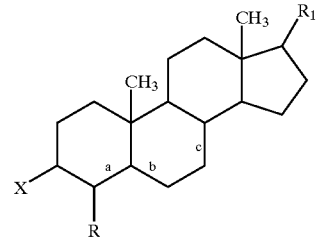

wherein
X is AR₂, oxo or thioxo;
R₁ is hydrogen, A₁R₃, oxo or thioxo,
—CH(R₄)CH₂CH₂CH(R₅)CHR₆R₇,
—CH(R₄)CH=CHCH(R₅)CHR₆R₇,
—CH(R₄)CH₂CH₂C(CHR₆R₇)=CHR₅, or
—CH(R₄)CH=CHC(CHR₆R₇)=CHR₅;
A and A₁ are each independently O or S;
R, R₂, R₃ and R₅ are each independently hydrogen or C₁–C₄alkyl; and $R_4$, $R_6$ and $R_7$ are each independently $C_1$–$C_4$alkyl;

provided that one of the bonds designated as a, b or c is a double bond and the other designated bonds are single bonds, and the optical isomers thereof, and the cis and trans isomers thereof; and a bait matrix.

21. A composition comprising a bait matrix; an effective termite attractive amount of a compound having the structural formula

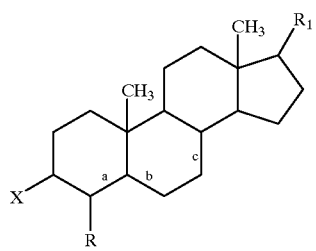

wherein

X is $AR_2$, oxo or thioxo;

$R_1$ is hydrogen, $A_1R_3$, oxo or thioxo,
—$CH(R_4)CH_2CH_2CH(R_5)CHR_6R_7$,
—$CH(R_4)CH$=$CHCH(R_5)CHR_6R_7$,
—$CH(R_4)CH_2CH_2C(CHR_6R_7)$=$CHR_5$, or
—$CH(R_4)CH$=$CHC(CHR_6R_7)$=$CHR_5$;

A and $A_1$ are each independently O or S;

R, $R_2$, $R_3$ and $R_5$ are each independently hydrogen or $C_1$–$C_4$alkyl; and $R_4$, $R_6$ and $R_7$ are each independently $C_1$–$C_4$alkyl;

provided that one of the bonds designated as a, b or c is a double bond and the other designated bonds are single bonds, and the optical isomers thereof, and the cis and trans isomers thereof; and an insecticide selected from the group consisting of a slow-acting toxicant, insect growth regulant and juvenile hormone accelerator.

22. A composition comprising an attractant for an insect, a pesticide and at least one additive selected from the group consisting of a bait matrix and excipient, the insect selected from the group consisting of coleoptera, hymenoptera and isoptera, and the attractant consisting essentially of an effective insect attractive amount of a compound having the structural formula

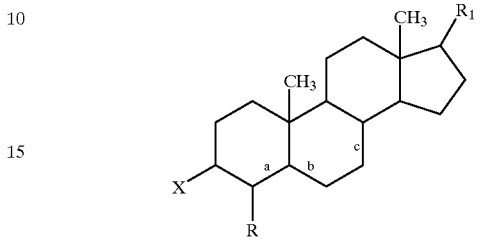

wherein

X is $AR_2$, oxo or thioxo:

$R_1$ is hydrogen, $A_1R_3$, oxo or thioxo,
—$CH(R_4)CH_2CH_2CH(R_5)CHR_6R_7$,
—$CH(R_4)CH$=$CHCH(R_5)CHR_6R_7$,
—$CH(R_4)CH_2CH_2C(CHR_6R_7)$=$CHR_5$, or
—$CH(R_4)CH$=$CHC(CHR_6R_7)$=$CHR_5$;

A and $A_1$ are each independently O or S;

R, $R_2$, $R_3$ and $R_5$ are each independently hydrogen or $C_1$–$C_4$alkyl; and $R_4$, $R_6$ and $R_7$ are each independently $C_1$–$C_4$alkyl;

provided that one of the bonds designated as a, b or c is a double bond and the other designated bonds are single bonds, and the optical isomers thereof, and the cis and trans isomers thereof.

* * * * *